United States Patent [19]
Törmälä et al.

[11] Patent Number: 6,010,513
[45] Date of Patent: Jan. 4, 2000

[54] DEVICE FOR INSTALLING A TISSUE FASTENER

[75] Inventors: Pertti Törmälä, Tampere; Olli Karhi, Oulu; Markku Tamminmaki, Tampere, all of Finland

[73] Assignee: Bionx Implants Oy, Tampere, Finland

[21] Appl. No.: 08/979,872

[22] Filed: Nov. 26, 1997

[51] Int. Cl.$^7$ .................................................. A61B 17/10
[52] U.S. Cl. ......................... 606/142; 606/143; 606/75; 606/219
[58] Field of Search ...................... 606/142, 143, 606/75, 219, 220, 213–221; 227/175.1, 175.3, 176.1, 177.1, 179.1

[56] References Cited

U.S. PATENT DOCUMENTS

| | | |
|---|---|---|
| 2,222,125 | 11/1940 | Stehlik . |
| 2,638,901 | 5/1953 | Sugarbaker . |
| 2,716,813 | 9/1955 | Smyres . |
| 3,075,199 | 1/1963 | Rose et al. . |
| 3,155,980 | 11/1964 | Mulno et al. . |
| 3,302,840 | 2/1967 | Sekiguchi et al. . |
| 3,923,225 | 12/1975 | Maier et al. . |
| 3,923,226 | 12/1975 | Maier . |
| 4,091,981 | 5/1978 | Moriguchi et al. . |
| 4,227,637 | 10/1980 | Haytayan . |
| 4,272,002 | 6/1981 | Moshofsky . |
| 4,530,453 | 7/1985 | Green . |
| 4,589,582 | 5/1986 | Bilotti . |
| 4,684,051 | 8/1987 | Akopov et al. . |
| 4,784,306 | 11/1988 | Baum . |
| 4,804,127 | 2/1989 | Kirkman . |
| 4,805,823 | 2/1989 | Rothfuss . |
| 4,932,580 | 6/1990 | Pfister et al. . |
| 4,991,763 | 2/1991 | Storace . |
| 5,135,152 | 8/1992 | Uno et al. . |
| 5,220,123 | 6/1993 | Oehry . |
| 5,251,532 | 10/1993 | Frommelt et al. . |
| 5,258,010 | 11/1993 | Green et al. . |
| 5,312,333 | 5/1994 | Churinetz et al. . |
| 5,452,835 | 9/1995 | Shkolnikov . |
| 5,522,533 | 6/1996 | Mukoyama et al. . |
| 5,558,264 | 9/1996 | Weinstein . |
| 5,575,054 | 11/1996 | Klinzing et al. . |
| 5,579,975 | 12/1996 | Moorman . |
| 5,605,272 | 2/1997 | Witt et al. . |
| 5,626,586 | 5/1997 | Pistl et al. ................................ 606/142 |
| 5,643,291 | 7/1997 | Pier et al. ................................ 606/142 |
| 8,202,852 | 9/1982 | Peters ...................................... 606/143 |

FOREIGN PATENT DOCUMENTS

| | | |
|---|---|---|
| 000 651 212 | 1/1993 | Australia . |
| 0 336 021 A1 | 10/1988 | European Pat. Off. . |
| 2 263 764 | 12/1972 | Germany . |
| 1 550 071 | 8/1979 | United Kingdom . |

*Primary Examiner*—Michael Buiz
*Assistant Examiner*—Lien Ngo
*Attorney, Agent, or Firm*—Kenyon & Kenyon

[57] ABSTRACT

The device of the present invention is designed for repairing a tear in soft and/or tough tissue of a patient, such as a tear in the meniscus of the knee.

The device has a conduit, such as a cannula, that may be easily inserted into the patient and through which the fastener is delivered to the patient. This conduit is aligned with a seat for holding a fastener and a means for pushing a fastener, such as a piston, so that the pushing means is capable of pushing a fastener from its seat, through the conduit and into the patient. In a preferred embodiment of the invention, the shape of the conduit exactly matches the shape of the cross-section of the fastener so that the surgeon may more accurately direct the angle and location at which the fastener enters the patient.

13 Claims, 6 Drawing Sheets

DASHED LINE: POSITION B AND D

DEVICE FOR INSTALLING A TISSUE FASTENER

FIELD OF THE INVENTION

This application is related to applicant's co-pending application No. 09/024,359.

This invention relates to the field of surgical devices. More specifically, this invention relates to an improved surgical device for inserting tissue fasteners.

The surgical device of the invention is particularly but not solely intended to be used in repair surgery of traumas of soft and/or tough tissues containing fibrous structures, such as knee meniscal tissues.

BACKGROUND OF THE INVENTION

In the past, doctors have effectively treated internal ruptures and tears of tissue by suturing, often with bioabsorbable sutures. For instance, this technique for treating ruptures of meniscal tissue in the knee has been described in N. A. Palmeri, T. F. Winters, A. E. Joiner and T. Evans, "The Development and Testing of the Arthroscopic Meniscal Staple", Arthroscopy, Vol. 5, No. 2, 1989, p. 156. However, suturing, particularly arthroscopic suturing, has many drawbacks. It is a complicated and tedious technique where risks for the patient are significant because of the danger to vessels and nerves. Additionally, the suturing of a ruptured meniscus leaves a single or several loops of sutures on the surface of the meniscal tissue, which can irritate joint cavity tissues. Therefore, for a long time surgeons have desired an absorbable fixation device, like a staple or fastener, which has the advantages of absorbable suturing techniques but which can be used more rapidly and safely than sutures.

Tissue fasteners have been developed, including fasteners that may be inserted entirely below the surface of the tissue that is being treated, thereby preventing any irritation that may result from the portion of the fastener remaining above the ruptured tissue surface. These fasteners are described in detail in U.S. patent application Ser. No. 08/887,130, entitled SURGICAL FASTENER FOR TISSUE TREATMENT, by Tormala, et al., which is hereby incorporated by reference.

Accordingly, there is a need for surgical devices to insert these fasteners. Such devices must be accurate, reliable, quick, easily positioned and operated within a patient, and cost effective. It is important to reduce the invasiveness and length of any surgery to repair internal ruptured tissues.

Certain previous devices for installing tissue fasteners require that the fasteners be manually inserted into the patient. It is time consuming for fasteners to be inserted with such devices because the surgeon has to, for instance, repeatedly tap the fastener until it is fully inserted into the patient. Further, because of the manual propulsion of the fastener, it is impossible with such devices to ensure that each fastener receives a measured, consistent amount of force to drive it into the patient.

Other previous devices for installing tissue fasteners have used mechanical techniques for propelling fasteners into a patient, but have only had the capability of holding one fastener at a time, thereby requiring the surgeon repeatedly during an operation to remove the device from the patient, load another fastener, and reinsert the device into the patient. It is important that a surgeon be able to insert these fasteners precisely. Thus, it is time consuming to remove the device from the patient and then reposition it so that it is in position to deliver a fastener exactly where needed. Having to do so increases the length and difficulty of the surgery, and the concomitant risk of infection or other complications to the patient.

There have also been devices for installing tissue fasteners that are capable of holding a fixed number of fasteners. These devices, however, are self contained and are not capable of receiving additional fasteners. These devices also do not provide enough flexibility to the surgeon concerning the number of fasteners used during the operation because in many cases, the surgeon will not know how many fasteners are needed until the operation has begun. For instance, if the device holds six fasteners, yet the operation demands eight fasteners, after the sixth fastener, the surgeon must remove the device, dispose of it, and insert a second new device containing another six fasteners into the patient. This device must then be disposed of after only two of its six fasteners have been inserted into the patient. The use of such a device increases the length and difficulty of the surgery, because the surgeon must change devices in the middle of the operation. This poses an added risk, because the second device could have slightly different operating characteristics than the first device to which the surgeon has become accustomed. Further, such devices are inefficient and costly because a single surgery could require the use of more than one delivery device. This is compounded by the fact that fasteners in the device that are not used are disposed of along with the delivery device.

Further, none of these devices provide a method for inserting fasteners in such a way that no part of the fastener remains on or above the surface of the tissue being treated. It is advantageous to be able to insert fasteners entirely below the surface of the tissue being treated to avoid any irritation or inflammation that could occur when other tissues rub against that portion of the fastener on or above the tissue that has been treated.

An additional problem with previous devices in this field is that their conduits are invariably straight or invariably curved. At times, a surgeon is required to use these devices to repair tissue that is difficult to reach. Further, a surgeon must precisely insert many different fasteners at different angles. Thus, at times, a straight conduit may be preferred, while at other times, it may be difficult for the surgeon to properly approach the tissue that is to be treated with a straight conduit and a curved conduit may be preferred. Presently, in such a situation, a surgeon would need to use entirely separate devices with different conduits to insert the different fasteners. Using entirely different devices during an operation poses the same risk as described previously—the second device could have slightly different operating characteristics than the first device to which the surgeon has become accustomed. This increases the risk that a fastener will not be optimally inserted. Further, such devices are inefficient and costly because a single surgery could require the use of more than one delivery device.

Thus, there is a desire in the field for a device to install tissue fasteners that is capable of holding more than one fastener and capable of receiving additional fasteners during an operation without requiring the surgeon to remove the device from the patient. With such a device, the surgeon may use as many fasteners as he requires, while only having to insert the device into the patient once. Also, no fasteners are wasted. This reduces the length, difficulty, and cost of the procedure. Further, there is a desire in the field for a device that is capable of inserting a fastener entirely within the tissue to be treated so that no part of the fastener remains above or on the surface of the tissue. Such a device reduces the likelihood of irritation and inflammation of the treated area. Also, there is a desire in the field for a device that accurately and reliably inserts fasteners. Lastly, there is a desire in the field for a device with a conduit that can be curved or straight, to allow the surgeon to more easily insert the fastener properly into the patient.

Thus, it is an object of the present invention to provide a device for installing tissue fasteners that allows a minimally invasive method for repairing torn or ruptured tissue.

It is further an object of the present invention to provide a device for installing tissue fasteners that is capable of holding more than one fastener and of receiving additional fasteners during an operation without requiring the removal of the device from the patient.

It is further an object of the present invention to provide a device for installing tissue fasteners that is capable of inserting a fastener entirely within the tissue being treated, so that no part of the fastener remains above or on the surface of the treated tissue.

It is further an object of the present invention to provide a device for installing tissue fasteners that may quickly and easily be positioned within a patient.

It is further an object of the present invention to provide a device for installing tissue fasteners that accurately and reliably inserts tissue fasteners into a patient.

It is further an object of the present invention to provide a device for installing tissue fasteners that is cost effective.

These objects and others are attained with the device of the present invention, as described below.

SUMMARY OF THE INVENTION

The device of the present invention is designed for repairing a tear in soft and/or tough tissue of a patient, such as a tear in the meniscus of the knee.

The device has a conduit, such as a cannula, that may be easily inserted into the patient and through which the fastener is delivered to the patient. This conduit is aligned with a seat for holding a fastener and a means for pushing a fastener, such as a piston, so that the pushing means is capable of pushing a fastener from its seat, through the conduit and into the patient. In a preferred embodiment of the invention, the shape of the conduit exactly matches the shape of the cross-section of the fastener so that the surgeon may more accurately direct the angle and location at which the fastener enters the patient. In another preferred embodiment, the pushing means may be made to slowly push the fastener from its seat and through the conduit until the distal end of the fastener contacts the surface of the tissue to be treated at the end of the conduit. At that time, the pushing means may be made to accelerate rapidly, thereby inserting the fastener into the tissue being treated. An advantage of this embodiment is that the fastener is less likely to become jammed in the conduit while being pushed slowly through it. Further, the conduit, piston, and fastener are subject to less wear, which helps to ensure proper functioning of the device during an operation.

The seat for holding fasteners is capable of holding a magazine containing one or more fasteners. When inserted into the seat, the magazine may be positioned so that a fastener is aligned with the pushing means and the conduit leading to the patient. Once a fastener has been inserted into the patient, the magazine may be manually positioned so that another fastener is shifted into position to be inserted. In one embodiment of this invention, the magazine may have means, such as a spring, for automatically moving a fastener into position for insertion once a fastener has been inserted.

The magazine may be easily removed from the seat during an operation, so that it may be replaced with a magazine containing one or more fasteners without requiring the conduit to be removed from the patient. Alternatively, the same magazine could be removed, refilled with one or more additional fasteners, and reinserted into the seat, without requiring the removal of the conduit from the patient. In yet another embodiment of the invention, when the magazine is positioned to allow the insertion of one fastener into the patient, a portion of the magazine is accessible to allow the insertion of one or more additional fasteners into the magazine. In this fashion, additional fasteners may be added to the magazine without requiring its removal from the device or the removal of the conduit of the device from the patient.

In a preferred embodiment of the invention, the conduit or barrel of the device is easily removable from the rest of the device. This allows the same device to be used during an operation with differently shaped conduits, depending upon the location and condition of the tissue being treated. Thus, for instance, during the same operation, the surgeon could insert fasteners through a straight conduit, then easily replace the straight conduit with a curved conduit and continue the operation without the need for an entirely new device.

In another preferred embodiment of the invention, the pushing means, e.g., piston, of the device is capable of extending slightly beyond the end of the conduit that is in contact with the tissue being treated. Such extension of the pushing means ensures that it pushes the fastener until it is embedded entirely within the tissue being treated, with no portion of the fastener remaining on or above the surface of the tissue being treated.

In yet another preferred embodiment of this invention, the device has a safety mechanism that helps prevent the surgeon from inadvertently shooting the fastener into the patient until the proper moment. This mechanism works in conjunction with the triggering mechanism so that the means for propelling the pushing means rapidly into the fastener cannot be actuated until both the triggering means and the safety mechanism are actuated simultaneously.

BRIEF DESCRIPTION OF THE DRAWINGS

The invention will be more fully described in conjunction with the accompanying drawings wherein.

DETAILED DESCRIPTION OF THE INVENTION

Figure 1:
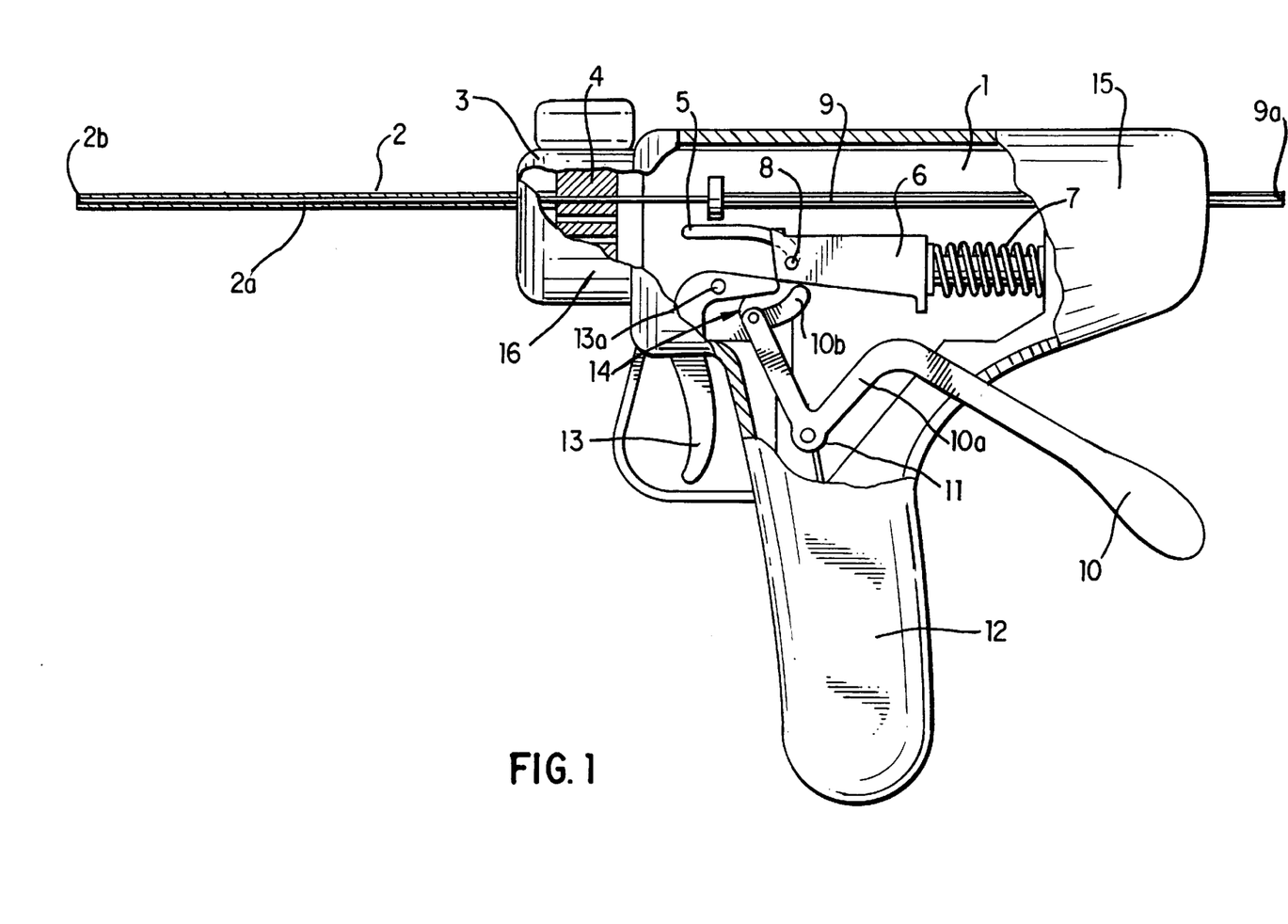
FIG. 1 is a side view, with parts broken away, of an embodiment of the device for installing tissue fasteners.

Referring to FIG. 1, demonstrating a particular embodiment of the present invention, the present invention comprises a conduit 2, containing an internal channel, 2a, through which a fastener may be pushed. The conduit 2 terminates distally at end 2b, which is where the fastener exits the conduit 2 and is inserted into the tissue being treated. Thus, during the insertion procedure, the end 2b is placed in contact with the tissue to be treated. In a preferred embodiment of the invention, the end 2b is not perpendicular to the conduit 2, but rather is angled to provide better contact with the tissue to be treated. The end 2b can be smooth, or can be rough or contain points or other means that oppose the movement of the end 2b laterally across the surface of the tissue to be treated. Such points or other corresponding structures at end 2b stabilize the end 2b by preventing it from inadvertently slipping across the tissue being treated once the surgeon has properly positioned the end 2b of the conduit 2 in contact with the tissue where the fastener is to be inserted. In one embodiment of the present invention, the points or corresponding structure at the end 2b of the conduit 2 are retractable, thereby allowing easy movement of the end 2b of the conduit 2 within the patient when retracted, yet preventing slippage of the end 2b of the conduit 2 when extended. Thus, for instance, a surgeon could have the points retracted while positioning the end 2b of the conduit 2 within the patient, and then extend the points once he has properly positioned the end 2 of the conduit 2b within the patient and is ready to insert the fastener.

Figure 2A:
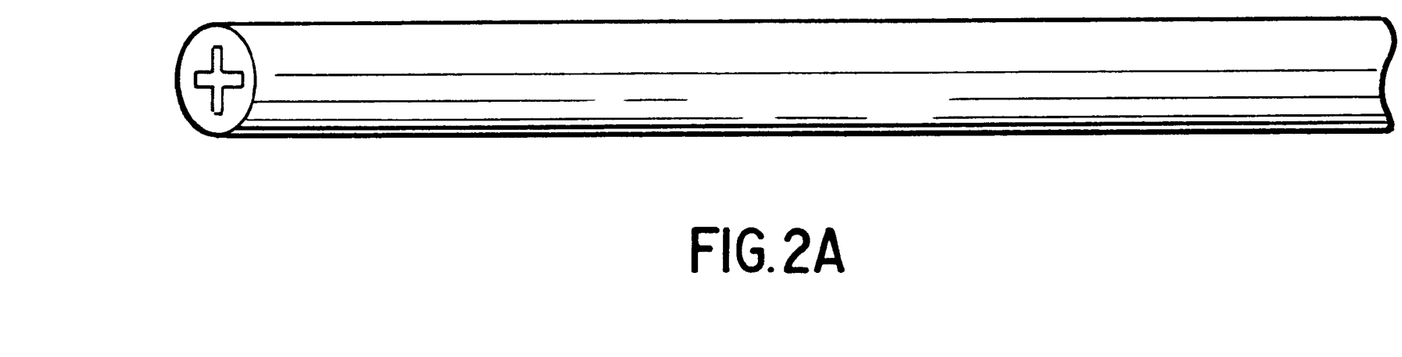
FIG. 2 is a perspective view of straight and curved conduits that may be used as part of the present invention.
Figure 2B:
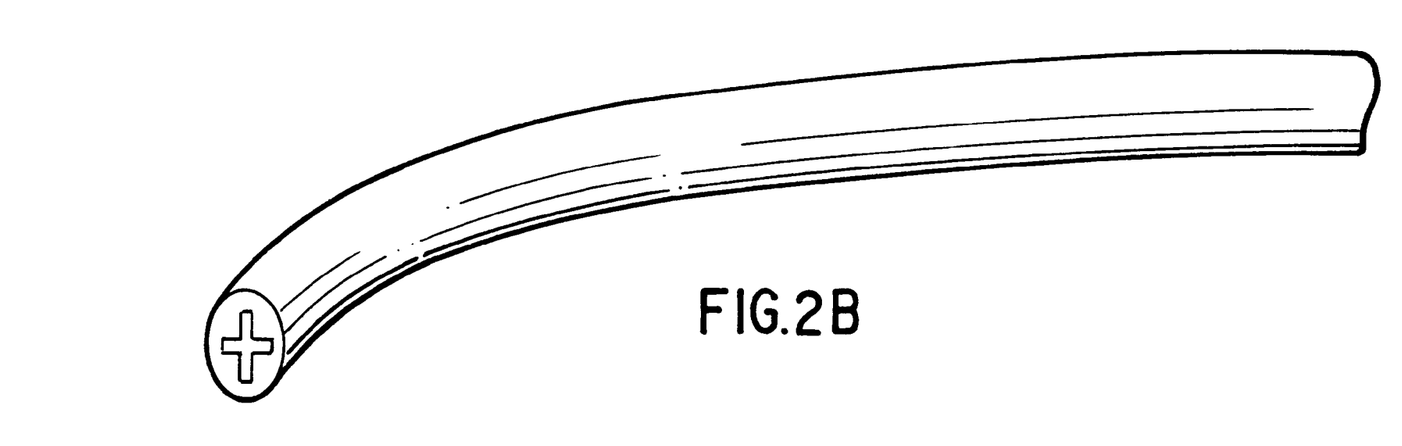

The geometry of the conduit 2 is variable, and will depend upon the type and location of the tissue being treated. FIG. 2 demonstrates in side view two possible geometries for conduit 2. In a typical embodiment, the conduit 2 will have an elongated shape and a cross section that may vary depending upon the type and location of tissue to be treated. For instance, the conduit may have a circular or ellipsoidal cross section. The conduit 2 can be straight or contain gradual curves to allow easier, less invasive positioning of the end 2b within the patient.

The shape of the internal channel 2a is variable, and will depend upon the shape of the fastener being inserted. Preferably, the shape of the internal channel 2a is the same as the shape of the cross section of the fastener. This allows for accurate control of the angle and location of insertion of the fastener. The particular internal channels in FIG. 2 are for use with fasteners having a cross-shaped cross section.

Referring again to FIG. 1, in one preferred embodiment of the present invention, the conduit 2 is easily removable from the body 1 of the device 15. This enables a surgeon to conveniently replace a conduit during an operation in order to allow easier, quicker, less invasive positioning of fasteners. For instance, it may be advantageous to use a straight conduit for the insertion of some fasteners during an operation and advantageous to use a curved conduit for the insertion of other fasteners during the same operation. With the present invention, the surgeon can simply remove the straight conduit from the body of the device and replace it with a curved conduit and continue the operation. This affords the surgeon great flexibility and helps to insure that the surgery will be as quick and minimally invasive as possible, as well as cost efficient. The conduit 2 may be releasably attached to the body 1 at its proximal end by any of several methods that are well known for the releasable attachment of mechanical parts. For instance, the body 1 may contain a simple spring loaded release that, when compressed or pulled or otherwise manipulated, allows the removal and insertion of conduit 2, yet when left alone secures the conduit 2 within the body 1.

The proximal end of conduit 2 attaches to the body 1 near the fastener magazine seat 3. The magazine seat is capable of receiving a magazine 4 containing one or more fasteners. The magazine seat 3 is configured so that the magazine 4 may be easily positioned within the magazine seat 3 so that a fastener within the magazine 4 is aligned with the entrance to the internal channel 2a of the conduit 2. Once a fastener has been inserted into a patient, the magazine 4 may again be easily positioned within the magazine seat 3 so that another fastener contained within the magazine 4 is aligned with the entrance to the internal channel 2a of the conduit 2.

In a preferred embodiment of the invention, there is a magazine locking mechanism 16 that promotes alignment of the magazine 4 within the magazine seat 3 and ensures that, once aligned within the magazine seat 3, the magazine 4 does not inadvertently slip out of alignment. This magazine locking function can be achieved, for example, by a spring loaded ball bearing that slides against the side of the magazine 4 as it moves within the magazine seat 3. The side of the magazine 4 can contain slight indentations for receiving the spring loaded ball bearing when the magazine 4 is aligned. The presence of the spring loaded ball bearing in the indentation provides enough resistance to movement to prevent the magazine 4 from inadvertently slipping out of alignment, yet does not provide so much resistance that the surgeon cannot slide the magazine 4 within the magazine seat 3 to move another fastener into alignment. When the surgeon moves the magazine 4, the ball bearing slides out of the indentation and slides along the side of magazine 4 until it enters another indentation, signaling to the surgeon that the magazine is positioned so that another fastener is in proper alignment.

In one embodiment of the invention, after a fastener is inserted, the magazine 4 need not be manually positioned within the magazine seat 3 to align another fastener with the internal channel 2a of the conduit 2 because the magazine 4 contains means for automatically aligning another fastener once the previously-aligned fastener has been inserted. This means may be as simple as a spring contained within the magazine 4 that pushes the fasteners of the magazine sequentially into alignment for insertion.

Figure 3A:
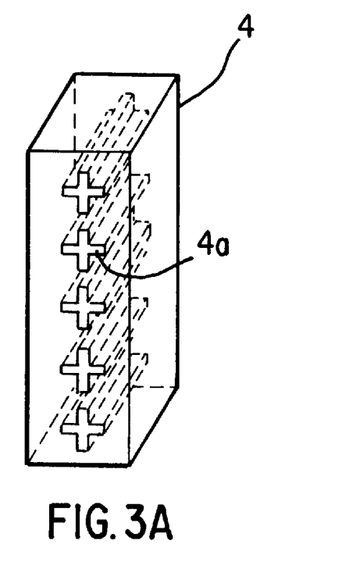
FIG. 3 is a perspective view of various magazines for holding fasteners that may by used as part of the present invention.
Figure 3B:
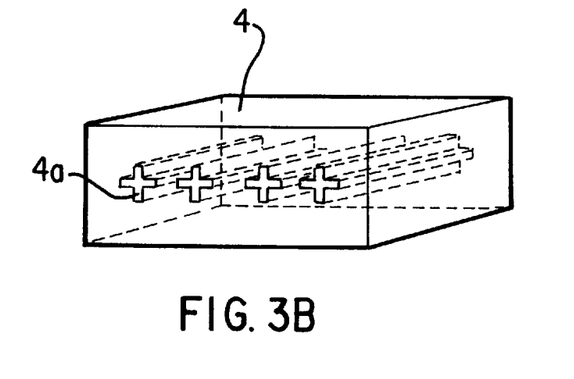
Figure 3C:
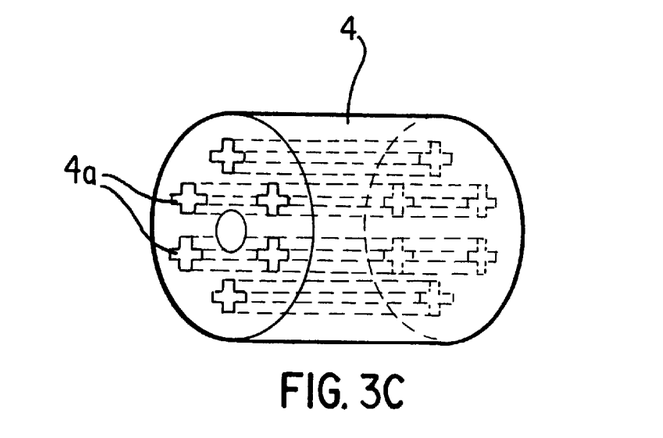

The magazine 4 and magazine seat 3 may have a variety of geometries. FIG. 3 demonstrates some potential geometries of magazines for use with this invention. It can be seen from FIGS. 3A and 3B that the magazine 4 may be box-shaped, with channels 4a for fasteners arranged linearly, either horizontally or vertically, within the magazine. Such box-shaped magazines may simply be pushed or pulled horizontally or vertically through or within the magazine seat in order to align a fastener for insertion. As shown in FIG. 3C, in another embodiment of the invention, the magazine 4 may be cylindrically shaped, with the channels 4a for fasteners arranged circularly within the magazine 4. Such cylindrical magazines may simply be rotated within the magazine seat in order to align a fastener for insertion. The particular magazines of FIG. 3 are for use with fasteners having a cross-shaped cross section, however the magazines may easily be configured to hold fasteners of various cross-sections.

Referring again to FIG. 1, in one preferred embodiment of the present invention, when the magazine 4 is aligned within the magazine seat 3, a portion of the magazine 4 remains accessible to the surgeon or other medical personnel for the insertion of additional fasteners to the magazine 4. Thus, if the surgeon has just inserted the last fastener within a magazine into the patient, he can have another fastener inserted into the magazine, without even having to remove the magazine from the device. The magazine may then be positioned so that the newly-inserted fastener is aligned for insertion. By so positioning the magazine to align the fastener, another portion of the magazine will now be accessible to the surgeon for the insertion of another fastener. Thus, after inserting the aligned fastener into the patient, another fastener may be inserted into the magazine, without the magazine being removed from the magazine seat. The magazine may be positioned so that the newly-inserted fastener is aligned for insertion. Such positioning will make another portion of the magazine accessible to the surgeon for the insertion of another fastener into the magazine. In this fashion, the surgeon may continually replenish the magazine and thereby use an unlimited number of fasteners during an operation, without ever having to entirely remove the magazine from the device.

When a fastener within the magazine 4 is aligned with the internal channel 2a of conduit 2, it is also aligned with the means for pushing the fastener through the internal channel 2a and into the patient. In the embodiment shown in FIG. 1, a piston 9 serves to push the fastener from the magazine 4, through the internal channel 2a, and into the patient. In the embodiment of FIG. 1, the proximal end 9a of the piston 9 extends out from the body 1 of the device so that the piston 9 may be positioned manually. When the piston 9 is fully retracted, i.e., when the piston 9 is located as far away from the conduit 2 as possible, the distal end of the piston 9 is located proximally of the magazine seat 3, thereby allowing the magazine 4 to be positioned so that a fastener is aligned with the piston 9 and the internal channel 2a of the conduit 2. The piston 9 is capable of sliding through the magazine 4 in the magazine seat 3, thereby pushing the aligned fastener from the magazine 4 into the conduit 2. When fully extended, the piston 9 reaches the distal end 2b of the conduit 2 and is thereby capable of pushing the fastener from the conduit 2 into the patient. In a preferred embodiment of this invention, the piston 9 is capable of extending slightly beyond the distal end 2b of the conduit 2, thereby allowing it to push a fastener entirely within the tissue being treated, so that no part of the fastener remains above or on the tissue surface.

The piston 9 may be accelerated in several different ways. In FIG. 1, the means for accelerating the piston 9 is a simple spring mechanism 7. Other possibilities include pneumatic, hydraulic, explosive, combustive, chemical or electromagnetic mechanisms. In FIG. 1, the spring 7 is attached to a striking pin 6, which is capable of traveling along a loop 5 and thereby striking and accelerating the piston 9. In a preferred embodiment of this invention, there is a safety means 14 which prevents the inadvertent acceleration of the striking pin 6 into the piston 9.

Figure 4:
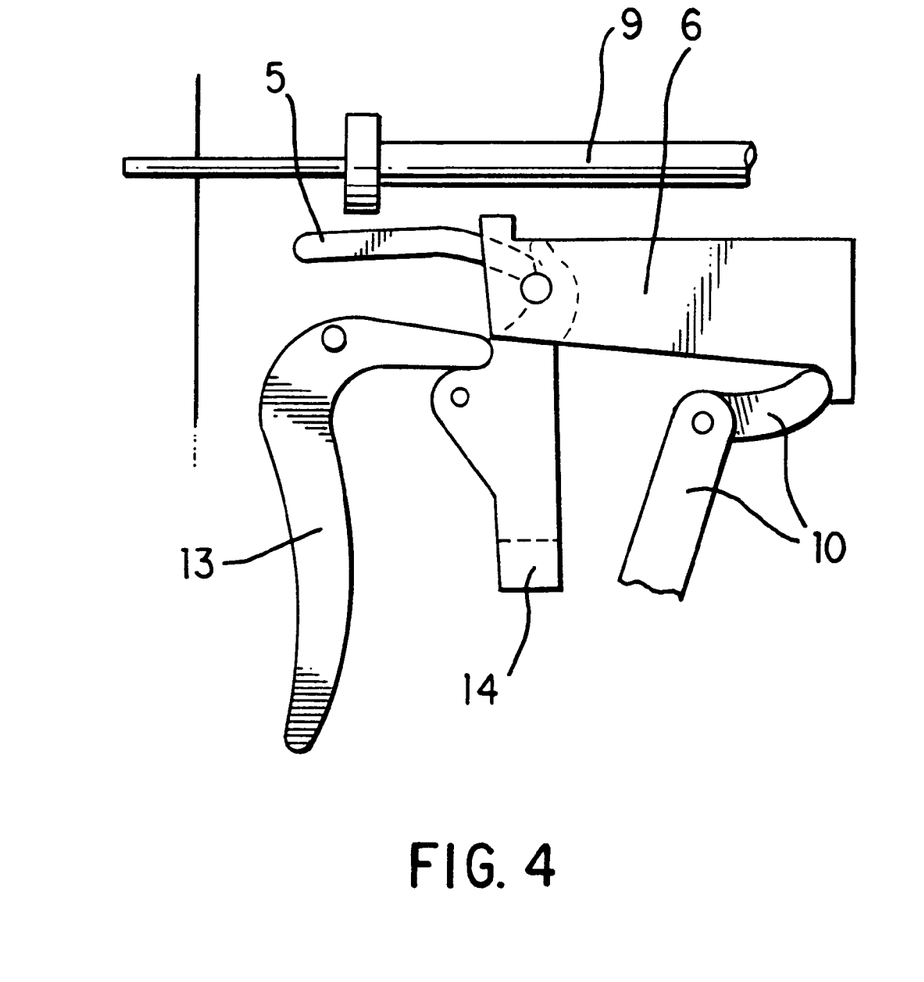
FIG. 4 is a side view of the striking pin portion of the device when being cocked.

The operation of the particular embodiment of FIG. 1 will now be described in detail. First, the spring mechanism 7 which is used to accelerate the piston 9 must be cocked. This is done by pushing the cocking lever 10 towards the handle 12 of the device. The cocking lever 10 pivots around point 10a, thereby causing the end 10b of the cocking lever to push the striking pin 6 in the proximal direction, thereby compressing the spring 7. The distal end of the striking pin 6 travels along the loop 5 in the proximal direction until it is pushed by the slanted end of the safety 14 into a notch 8 at the proximal end of the loop 5. When in the notch 8, the striking pin 6 cannot move distally. Thus, the spring 7 remains compressed. The safety 14 prevents the striking pin 6 from moving out of the notch 8, thereby preventing inadvertent release of the striking pin 6 and acceleration of the piston 9. FIG. 4 shows the relative positions of the cocking lever 10, striking pin 6, piston 9, safety 14, and trigger 13 just after the striking pin has been cocked. As seen on FIG. 1, the cocking lever 10 is returned to its previous position by a separate return spring 11.

Figure 6:
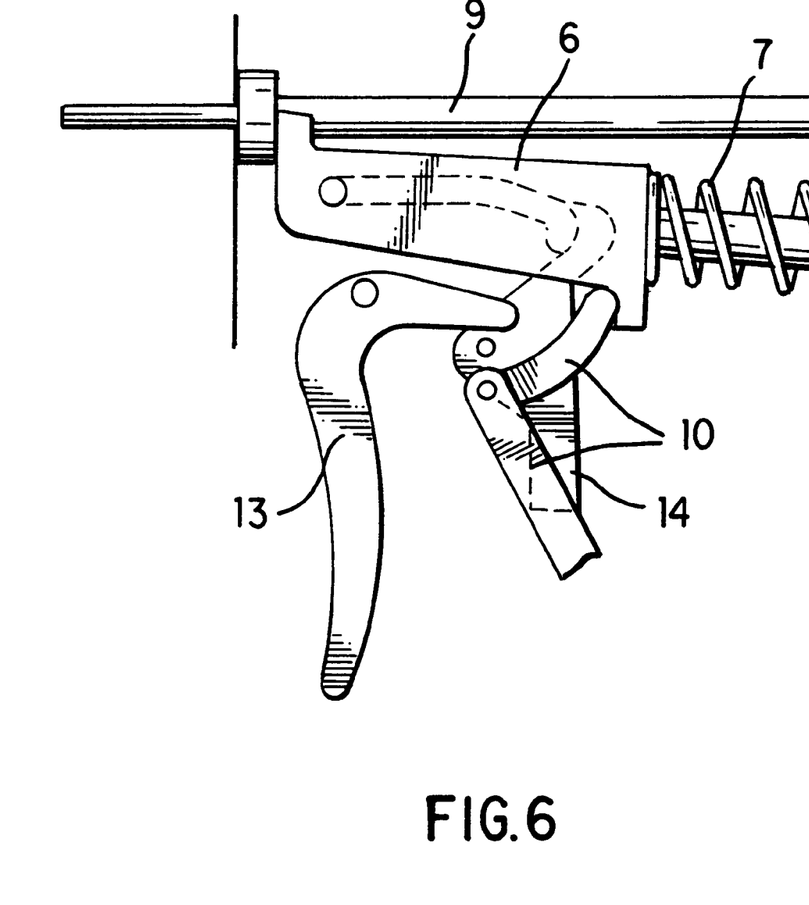
FIG. 6 is a side view of the striking pin that may be used as part of the present invention, as seen after inserting a fastener into a patient.

Referring to FIGS. 1, 4 and 6, when the striking pin 6 is in the cocked position, the piston 9 may be freely positioned by the surgeon. The surgeon pulls the piston 9 proximally, so that the distal end of the piston 9 is located proximally of the magazine seat 3. A magazine 4 is inserted into the magazine seat 3 and positioned so that a fastener is aligned with the internal channel 2a of the conduit 2 and the piston 9. After positioning the device properly within the patient, so that the distal end 2b of the conduit 2 is in contact with the tissue to be treated, the surgeon may then push the piston 9 distally, so that the distal end of the piston 9 travels through the magazine 4, thereby pushing the fastener into internal channel 2a of the conduit 2. The piston 9 may be pushed until the fastener reaches the distal end 2b of the conduit 2 and contacts the tissue to be treated.

Figure 5:
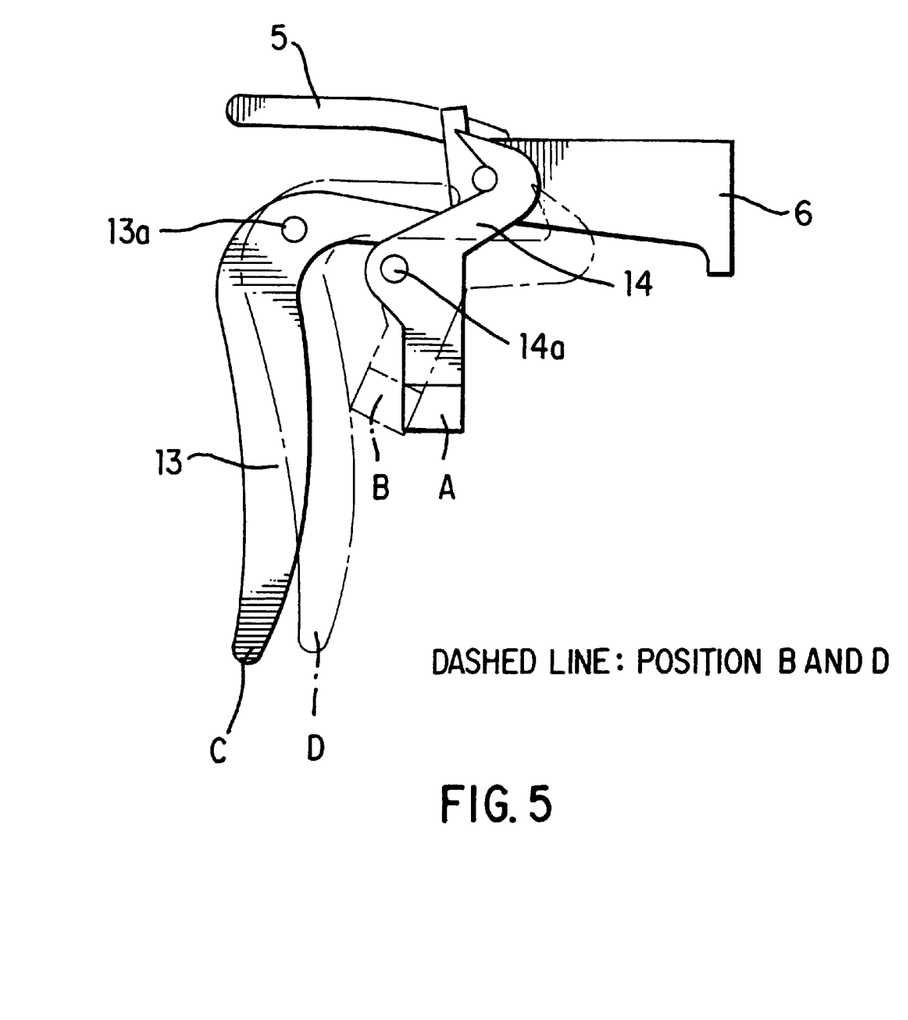
FIG. 5 is a side view of the striking pin, safety and triggering mechanisms that may be used as part of the present invention.

Referring to FIGS. 1 and 5, the surgeon must then release the safety 14 by pushing the safety lever 14 distally. When the safety 14 is in position A, the top end of the safety 14 holds the striking pin 6 in place in the notch 8 on the loop 5. When the safety lever 14 is moved distally to position B, the lever 14 pivots around point 14a, and the top of the safety lever 14 moves proximally and downward, thereby no longer preventing the striking pin 6 from moving distally and upward when moved out of the notch 8 on the loop 5 by the triggering means 13. While holding the safety lever in position B, the surgeon then pulls the trigger 13 proximally, from position C to position D as shown in FIG. 5. This causes the end of the trigger 13, which pivots around point 13a, to push the striking pin 6 off of the notch 8 on the loop 5. The striking pin 6, now removed from the notch 8, is accelerated rapidly along the loop 5 in the distal direction by the compressed spring 7. As it travels along the loop 5, the striking pin 6 strikes the piston 9, thereby accelerating it rapidly in the distal direction. The distal end of the piston 9 pushes the fastener into the tissue to be treated. The distal movement of the piston 9 stops once the distal end of the piston is at, or in a preferred embodiment of the invention, slightly beyond, the distal end 2b of the conduit 2. FIG. 6 shows the relative positions of the cocking lever 10, striking pin 6, piston 9, safety 14, and trigger 13 after the striking pin 6 has accelerated the piston 9 so that it has inserted a fastener into the patient.

In order to insert another fastener, the surgeon then merely repeats the above process, except that he need not insert another magazine, but rather merely reposition the magazine that has already been inserted into the device so that another fastener is aligned with the internal channel 2a of the conduit 2.

After the description above of the present invention and certain specific embodiments thereof, it will be readily apparent to those skilled in the art that many variations and modifications may be made to the present invention without departing from the spirit and scope thereof.

We claim:
1. A device for installing tissue fasteners into a patient, comprising:
  a conduit for delivering a fastener into the patient, said conduit having an interior shape and a distal end for insertion into the patient,
  a tissue fastener magazine, said magazine being capable of removably receiving one or more tissue fasteners,
  a body having a seat capable of removably receiving said tissue fastener magazine, so that each of said fasteners is capable of being aligned with said conduit while said distal end of said conduit is located within said patient, and means for moving said tissue fasteners from said seat into said conduit and the patient.

2. The device of claim 1, wherein said conduit is removably attached to said body.

3. The device of claim 1, further comprising a retractable stabilizer located on said distal end of said conduit.

4. The device of claim 1, wherein said means for moving said tissue fasteners comprises a piston.

5. The device of claim 4, wherein said piston is capable of sliding through said conduit and extending beyond said distal end of said conduit.

6. The device of claim 1, wherein the diameter of said interior shape of said conduit is the same as, or slightly greater than, the greatest cross section of said tissue fasteners.

7. The device of claim 1, wherein said magazine is capable of receiving at least one fastener while said magazine is located at least partially within said seat and while said distal end of said conduit is located within said patient.

8. The device of claim 1, wherein the means for moving said tissue fasteners is capable of moving fasteners at more than one speed.

9. The device of claim 8, wherein the means for moving said tissue fasteners is capable of moving said tissue fasteners at a faster rate from said distal end of said conduit into said patient than the rate of moving said fasteners from said magazine into said conduit.

10. The device of claim 4, wherein the means for moving said tissue fasteners is capable of moving fasteners at more than one speed.

11. The device of claim 10, wherein the means for moving said tissue fasteners is capable of moving said tissue fasteners at a faster rate from said distal end of said conduit into said patient than the rate of moving said fasteners from said magazine into said conduit.

12. A device for installing tissue fasteners in a patient, comprising:

a conduit for delivering a fastener into the patient, said conduit having an interior shape and a distal end for insertion into the patient, a tissue fastener magazine, said magazine being capable of removably receiving one or more tissue fasteners, a body having a seat capable of removably receiving said tissue fastener magazine, so that each of said fasteners is capable of being aligned with said conduit while said distal end of said conduit is located within said patient, means for moving said tissue fasteners from said seat into said conduit and the patient, a trigger for causing said means for moving to move said tissue fasteners from said conduit into the patient when the trigger is moved from a first position to a second position, and cocking means for moving said trigger from said second position to said first position when said cocking means is moved from an uncocked position to a cocked position.

13. The device of claim 11, further comprising spring means connected to said cocking means for automatically moving said cocking means from the cocked position to the uncocked position when the trigger is moved from the first position to the second position.

* * * * *